United States Patent
Minuth et al.

(10) Patent No.: US 7,166,842 B2
(45) Date of Patent: Jan. 23, 2007

(54) GAS SENSOR ARRANGEMENT WITH REDUCED SETTLING TIME

(75) Inventors: Rudi Minuth, Freising (DE); Joerg Fischer, Munich (DE); Thomas Tille, Munich (DE)

(73) Assignees: Tyco Electronics Raychem GmbH, Ottobrunn (DE); Bayerische Motoren Werke Aktiengesellschaft, Munich (DE)

( * ) Notice: Subject to any disclaimer, the term of this patent is extended or adjusted under 35 U.S.C. 154(b) by 99 days.

(21) Appl. No.: 11/148,944

(22) Filed: Jun. 9, 2005

(65) Prior Publication Data

US 2006/0011842 A1    Jan. 19, 2006

(30) Foreign Application Priority Data

Jun. 9, 2004   (DE) ................ 10 2004 028 077

(51) Int. Cl.
G01N 21/00    (2006.01)

(52) U.S. Cl. ............... 250/339.13; 250/345; 250/351; 250/350; 250/343; 250/352; 250/343.03; 250/343.04

(58) Field of Classification Search ........... 250/339.03, 250/350
See application file for complete search history.

(56) References Cited

U.S. PATENT DOCUMENTS

| | | | |
|---|---|---|---|
| 4,101,221 A | 7/1978 | Schunck et al. | |
| 4,954,718 A | 9/1990 | Mattheissen | |
| 5,070,244 A | 12/1991 | Simpson ............ | 250/343 |
| 5,291,884 A | 3/1994 | Heinemann et al. | |
| 5,424,545 A * | 6/1995 | Block et al. .......... | 250/343 |
| 5,608,219 A | 3/1997 | Aucremanne .......... | 250/343 |
| 5,936,714 A | 8/1999 | Gibbs | |
| 6,067,840 A | 5/2000 | Chelvayohan et al. ... | 73/23.2 |
| 6,694,800 B1 * | 2/2004 | Weckstrom et al. ..... | 73/25.01 |

FOREIGN PATENT DOCUMENTS

| | | |
|---|---|---|
| DE | 2225 319 | 12/1972 |
| DE | 36 15 259 A1 | 11/1987 |
| DE | 44 38 244 C1 | 3/1996 |
| DE | 195 20 488 C1 | 9/1996 |
| DE | 199 22 590 A1 | 9/2000 |
| DE | 199 25 196 C2 | 12/2000 |
| DE | 102 21 708 A1 | 12/2003 |
| EP | 0 616 207 A2 | 9/1994 |
| GB | 2317010 A * | 3/1998 |
| WO | WO 00/55603 | 9/2000 |

OTHER PUBLICATIONS

Search Report dated Aug. 25, 2004 for application No. DE 10 2004 028 077.0.
European Search Report for Application No. EP 05 01 2030 dated Aug. 25, 2005, mailed Sep. 2, 2005.

* cited by examiner

*Primary Examiner*—David Porta
*Assistant Examiner*—Djura Malevic
(74) *Attorney, Agent, or Firm*—Barley Snyder LLC

(57) ABSTRACT

A gas sensor arrangement for detecting the presence or concentration of an analyte in a measuring gas comprises a gas measuring chamber having an inlet for receiving the measuring gas. A measuring radiation source is arranged in the gas measuring chamber. The measuring radiation source emits radiation in a non-uniform pulse sequence according to a signal from a controller. A radiation detector receives the radiation emitted from the measuring radiation source. The radiation detector sends an output signal to the controller for processing.

10 Claims, 6 Drawing Sheets

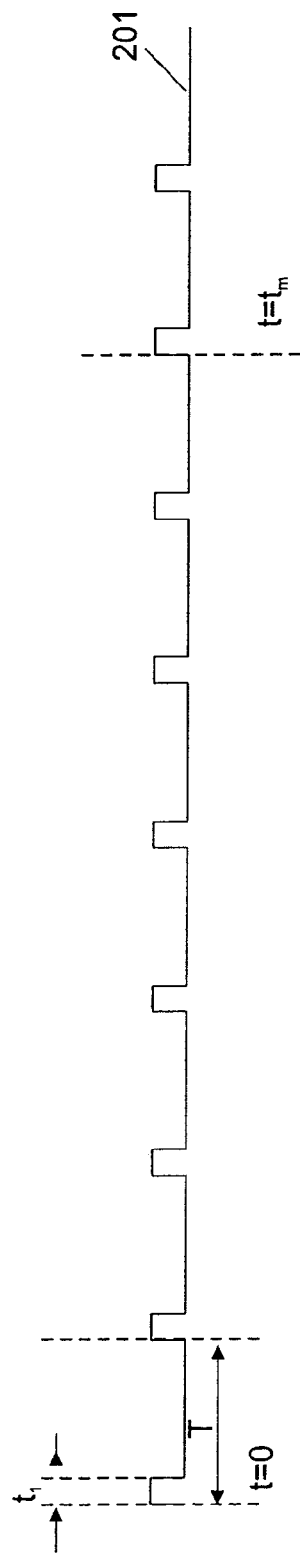
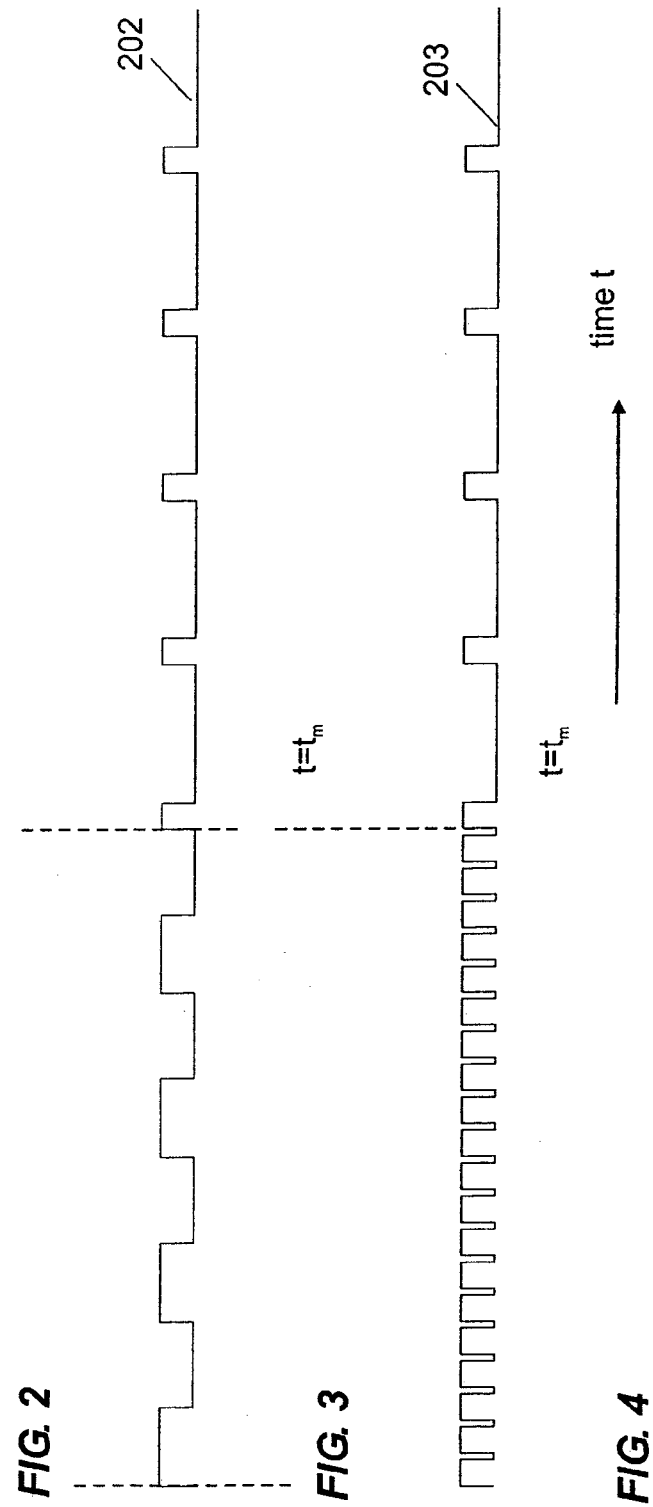
*Prior Art*
FIG. 2
FIG. 3
FIG. 4

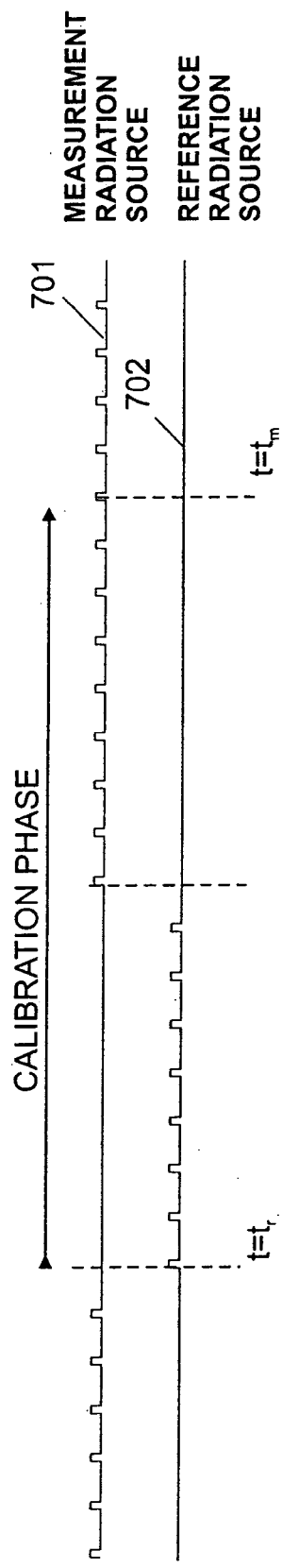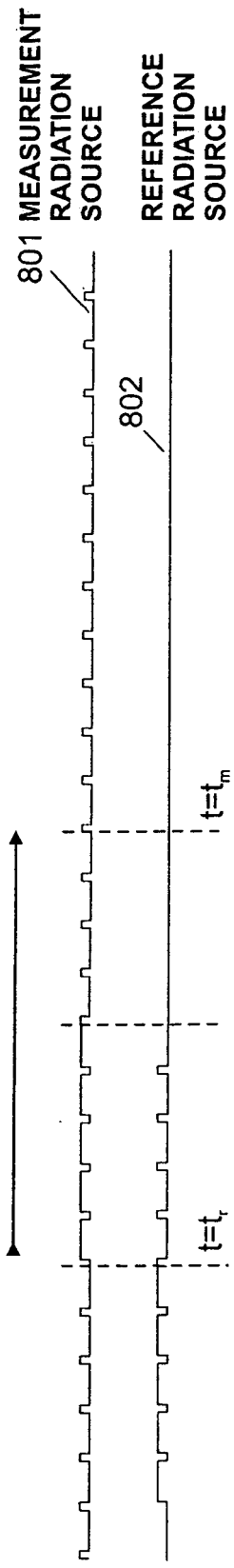
FIG. 7
FIG. 8

GAS SENSOR ARRANGEMENT WITH REDUCED SETTLING TIME

FIELD OF THE INVENTION

The invention relates to a gas sensor arrangement comprising at least a measuring radiation source, a gas measuring chamber, and a radiation detector wherein the radiation detector generates an output signal dependant on the presence and/or concentration of an analyte in a measuring gas in the gas measuring chamber.

BACKGROUND OF THE INVENTION

Gas sensor arrangements for detecting a wide variety of analytes, for example methane or carbon dioxide, are well known. Examples of such gas sensors are disclosed in EP 0 616 207 A2, WO 00/55603 A1, and DE 199 251 96 C2. The gas sensors comprise a measuring radiation source, a gas measuring chamber, and a radiation detector. The gas sensors are based on the principle that a large number of polyatomic gases absorb radiation, particularly in an infrared wavelength range. The absorption occurs at a wavelength characteristic for the gas, for example at 4.24 µm for carbon dioxide. Using gas sensors, it is therefore possible to detect the existence of a gas component and/or the concentration of the gas component in a measuring gas. The intensity of the radiation measured by the radiation detector is, in accordance with the known Beer-Lambert law, a measure of the concentration of the measuring gas. In a non-dispersive infrared (NDIR) sensor, for example, a broadband radiation source may be used and the wavelength of interest adjusted via an interference filter or grid. Alternatively, a selective radiation source may be used, for example a light-emitting diode or a laser, in combination with non-wavelength-selective radiation receivers.

The use of gas sensor arrangements to detect, for example, carbon dioxide is important in a large number of applications. For example, gas sensor arrangements can be used to monitor and regulate the quality of interior air, the cleaning cycle of self-cleaning ovens, the supply of carbon dioxide to plants in greenhouses, and the breathing air of a patient. Additionally, gas sensor arrangements can be used in warning systems to detect, for example, leaking carbon dioxide, such as in air conditioning systems.

In the automotive field, gas sensor arrangements can be used, for example, to monitor the carbon dioxide content of the interior air to increase the energy efficiency of the heating and air conditioning systems. For example, to increase energy efficiency during heating and air conditioning, the carbon dioxide content of the air in the interior of the vehicle is monitored. In the event that an increase in carbon dioxide concentration occurs, a supply of fresh air is introduced via a fan flap. Additionally, modern air conditioning systems are based on carbon dioxide coolants. The gas sensors can therefore fulfil a monitoring function in conjunction with issuing carbon dioxide in the event of potential defects. Gas sensors of this type, however, must meet stringent requirements with respect to ruggedness, reliability, and miniaturization.

One example of a gas sensor arrangement is shown in EP 0 616 207 A2. In this gas sensor arrangement, the measuring radiation source is not operated uniformly but pulsed with a specific frequency. A constant frequency and a specific pulse duty factor are normally selected. The pulse duty factor identifies the ratio of operating time (pulse width) to periodic time. A narrow band filter in the radiation detector region can reduce interference during signal processing. The frequency of the filter corresponds to the pulse frequency with which the measuring radiation source is pulsed.

These types of gas sensor arrangements have a crucial disadvantage in that when the measuring radiation source is switched-on, the settling time or period until usable measurement results are available is relatively long, because only a relatively small amount of energy is radiated per pulse. This is also the case in gas sensor arrangements having operating modes, where the measuring radiation source emits no radiation for a relatively long period.

For example, FIG. 2 shows a conventional uniform pulse sequence for a conventional gas sensor arrangement with a pulse duty factor $t1/T$ of 0.16, a periodic time of $T=2.5$ seconds, and a pulse width of 0.4 seconds. At time $t=0$, the conventional gas sensor arrangement is switched-on and the measuring radiation source begins to emit pulses according to curve 201 (a bottom level of the curve 201 indicates the switched-off state and a top level of the curve 201 indicates a switched-on state). After being switched-on, however, the conventional gas sensor arrangement has to settle thermally, which takes about 10–15 measurement values. Actual measurements, therefore, can not begin until the settled state is reached at about time $t=tm$. Thus, the first 10–15 measurement values are not usable. This is particularly problematic in safety applications, where the gas sensor arrangement has to be frequently switched-on and off.

Another example of a gas sensor arrangement is shown in DE 199 25 196 C2. In this gas sensor arrangement, a reference radiation source is provided in addition to a measuring radiation source. The reference radiation source is switched-on periodically to monitor the aging of the measuring radiation source. The reference radiation source is not used for normal measurement, but is operated at large monitoring intervals for a short duration to detect the aging of the measuring radiation source. The operation of the reference radiation source at large monitoring intervals for only a short duration is necessary so that the aging of the reference radiation source is disregarded.

In these types of gas sensor arrangements, the settling time or period until usable measurement results are available is also relatively long after having been switched-off. For example, FIG. 7 shows a conventional pulse sequence for a reference radiation source and a measuring radiation source. Curve 701 denotes the pulse sequence for the measuring radiation source and curve 702 denotes the pulse sequence for the reference radiation source. In principle, the reference radiation source is only switched-on for referencing. In FIG. 7, the reference radiation source is switched-on at time $t=tr$. When the reference radiation source is first switched-on, it requires a certain amount of time until thermal equilibrium is established and reliable measurement values can be delivered.

At time $t=tm$, the measuring radiation source is again switched-on to continue measurement and at the same time to detect comparative values for correction. Because the measuring radiation source was switched-off during the time in which the reference radiation source was pulsed, the settled state for the measuring radiation source must also now be re-established.

It is commonly assumed that approximately four measurement values are required to reach the settled state and approximately four measurement values are required for referencing for a total of eight pulses. The referencing therefore lasts for 16 measuring cycles with unaltered pulse sequences being emitted. If approximately three seconds are calculated, for example, per measuring cycle, the entire referencing process lasts at least 48 seconds. There is therefore a total of 48 seconds during which no measurement data which can be utilized in a warning system. As a result, a considerable amount of gas could escape unnoticed through a gas leak during the referencing phase.

SUMMARY OF THE INVENTION

It is therefore an object of the invention to provide a gas sensor arrangement where the settling time of the gas sensor arrangement is reduced, and the reliability of the gas sensor arrangement is increased.

This and other objects are achieved by a gas sensor arrangement for detecting the presence or concentration of an analyte in a measuring gas comprising a gas measuring chamber having an inlet for receiving a measuring gas. A measuring radiation source is arranged in the gas measuring chamber. The measuring radiation source emits radiation in a non-uniform pulse sequence according to a signal from a controller. A radiation detector receives the radiation emitted from the measuring radiation source. The radiation detector sends an output signal to the controller for processing.

BRIEF DESCRIPTION OF THE DRAWINGS

FIG. 2 is a diagram of conventional uniform pulse sequence according to the prior art;

FIG. 3 is a diagram of a first pulse sequence according to the invention;

FIG. 4 is a diagram of a second pulse sequence according to the invention;

FIG. 7 is a diagram of conventional referencing sequence according to the prior art;

FIG. 8 is a diagram of a referencing sequence according to the invention; and

DETAILED DESCRIPTION OF THE INVENTION

Figure 1:
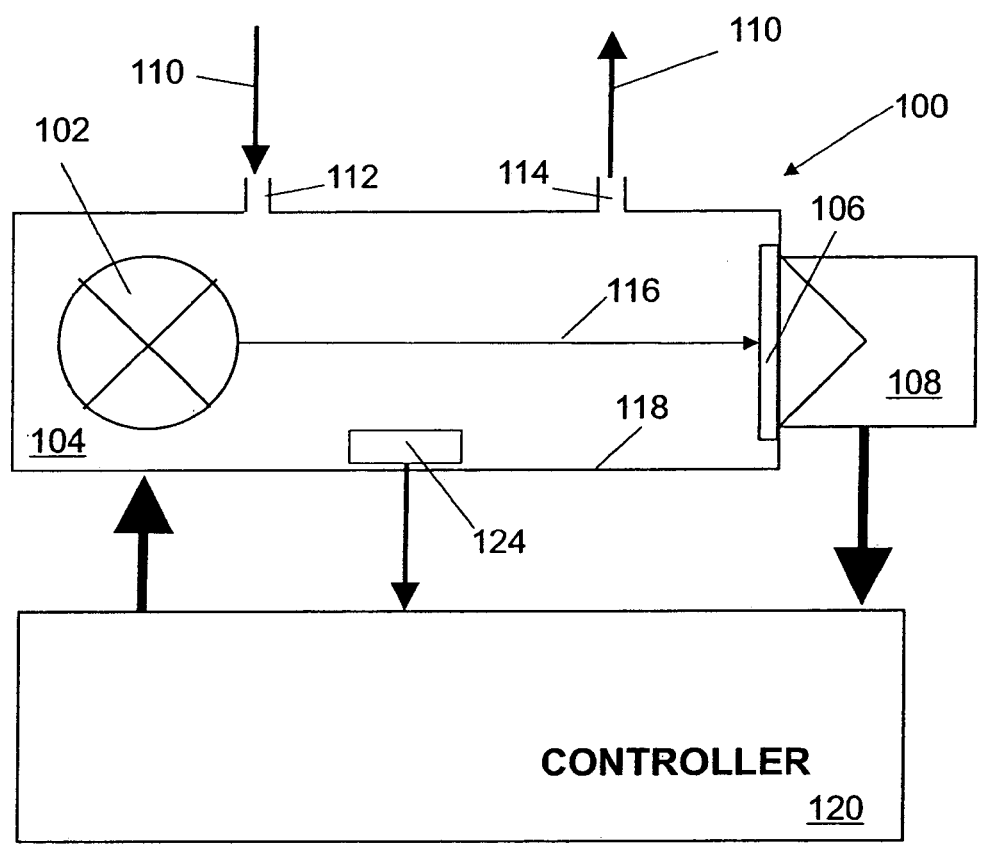
FIG. 1 is a diagrammatic view of a gas sensor arrangement according to a first embodiment of the invention.

FIG. 1 shows a gas sensor arrangement 100 according to a first embodiment of the invention. As shown in FIG. 1, the gas sensor arrangement 100 comprises a measuring radiation source 102, a gas measuring chamber 104, an optical wavelength filter 106, and a radiation detector 108. The gas sensor arrangement 100 may be, for example, a non-dispersive infrared (NDIR) sensor where the measuring radiation source 102 is a broadband infrared radiation source and the radiation detector 108 detects infrared radiation.

The gas measuring chamber 104 includes an inlet 112 and an outlet 114. A measuring gas 110 is pumped into the gas measuring chamber 104 through the inlet 112 or diffused therein. The measuring gas 110 contains at least one analyte. The concentration of the measuring gas 110 can be determined electro-optically via the absorption of a specific wavelength in the infrared range. A temperature sensor 124 may be provided to detect the temperature in the gas measuring chamber 104.

Radiation 116 emitted from the measuring radiation source 102 is directed through the gas measuring chamber 104 to the radiation detector 108. In order to improve measuring, energy efficiency, and accuracy and to accelerate thermal equilibrium by specific heating of an inner wall 118 of the gas measuring chamber 104, an inner wall 118 of the gas measuring chamber 104 may be configured such that it reflects the radiation 116 emitted by the measuring radiation source 102. For example, the inner wall 118 of the gas measuring chamber 104 may be formed of a radiation reflecting plastic material or coated with a metal material, such as gold, by sputtering, vapor coating, or electroplating.

Figure 5:
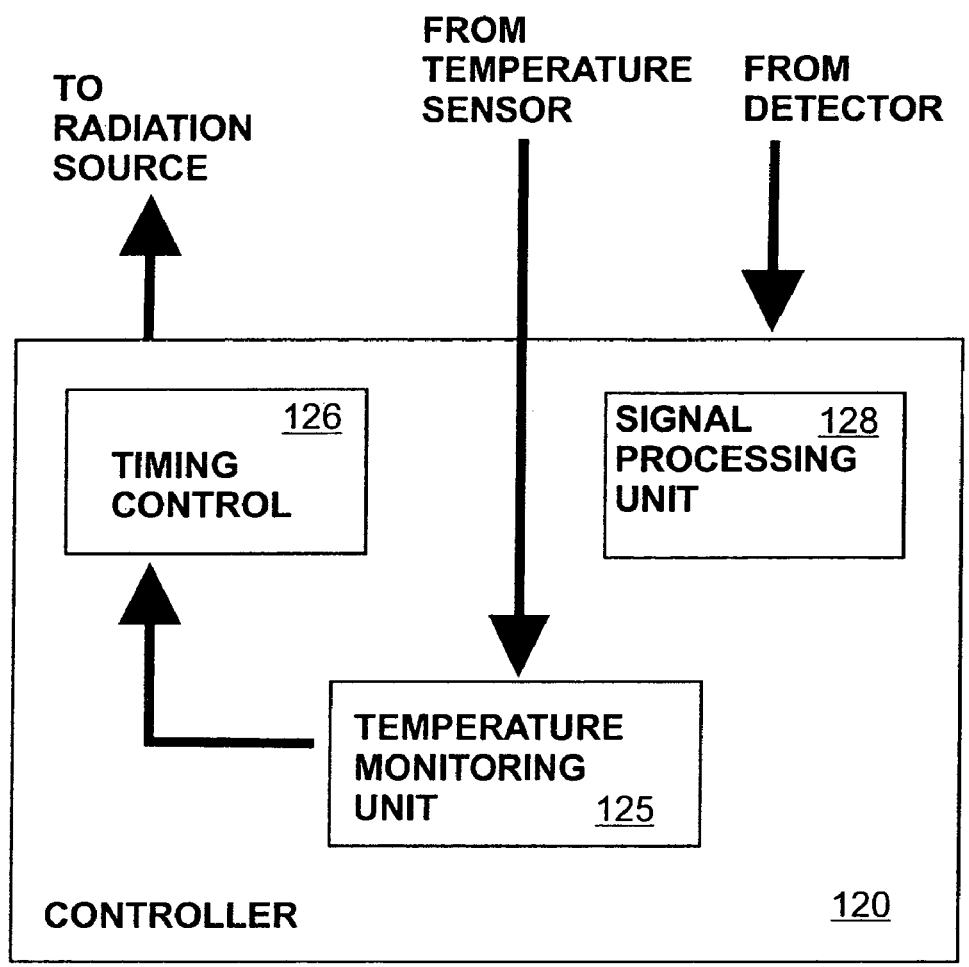
FIG. 5 is a diagrammatic view of a controller of the gas sensor arrangement shown in FIG. 1.

The radiation detector 108 includes the optical wavelength filter 106. The optical wavelength filter 106 only allows through to the radiation detector 107 a wavelength range that gas molecules in the measuring gas 110 absorb. Other gas molecules generally do not absorb radiation at this wavelength and therefore do not influence the amount of the radiation 116 that reaches the radiation detector 108. A controller 120 controls the measuring radiation source 102 and receives output signals from the radiation detector 108 for processing. As shown in FIG. 5, the controller 120 comprises a timing control 126, a signal processing unit 128, a temperature monitoring unit 125, and/or a timer (not shown). The timing control 126 controls the operation of the measuring radiation source 102. The signal processing unit 128 receives and processes the output signals delivered by the radiation detector 108. A frequency filter (not shown) may be provided, which is aligned with the pulse frequency in order to improve the elimination of background signals during measurement. The signal processing unit 128 can also supply signals to warning devices and display devices to show measurement results. The temperature monitoring unit 125 and/or the timer can be provided to determine when a warming-up operation is to be switched to a measuring operation by determining when a settled state has been reached.

The radiation 116 is pulsed by the measuring radiation source 102 in order to be able to filter out thermal background signals from a desired signal. FIGS. 3–4 show pulse sequences according to first and second embodiments of the invention. As shown by curve 202 in FIG. 3, the settled state can be reached earlier by increasing the duration of the first four pulses, so that the pulse duty factor is increased. After reaching the settled state at time t=tm, a conventional uniform pulse sequence is resumed. Reliable measurement values can therefore be obtained substantially earlier than with the conventional uniform pulse sequence shown in FIG. 2. As shown by curve 203 in FIG. 4, a further possibility to reach the settled state more quickly is to leave pulse width t1 unaltered and increase the frequency of the pulse. In principle, any pulse duty factors and frequencies can be used before the start of actual measuring. The settling process is always purposefully influenced, such that its duration is reduced and usable measurement values are available earlier. The specific pulse sequence used before the start of actual measuring is system-dependent and can be detected empirically.

Figure 6:
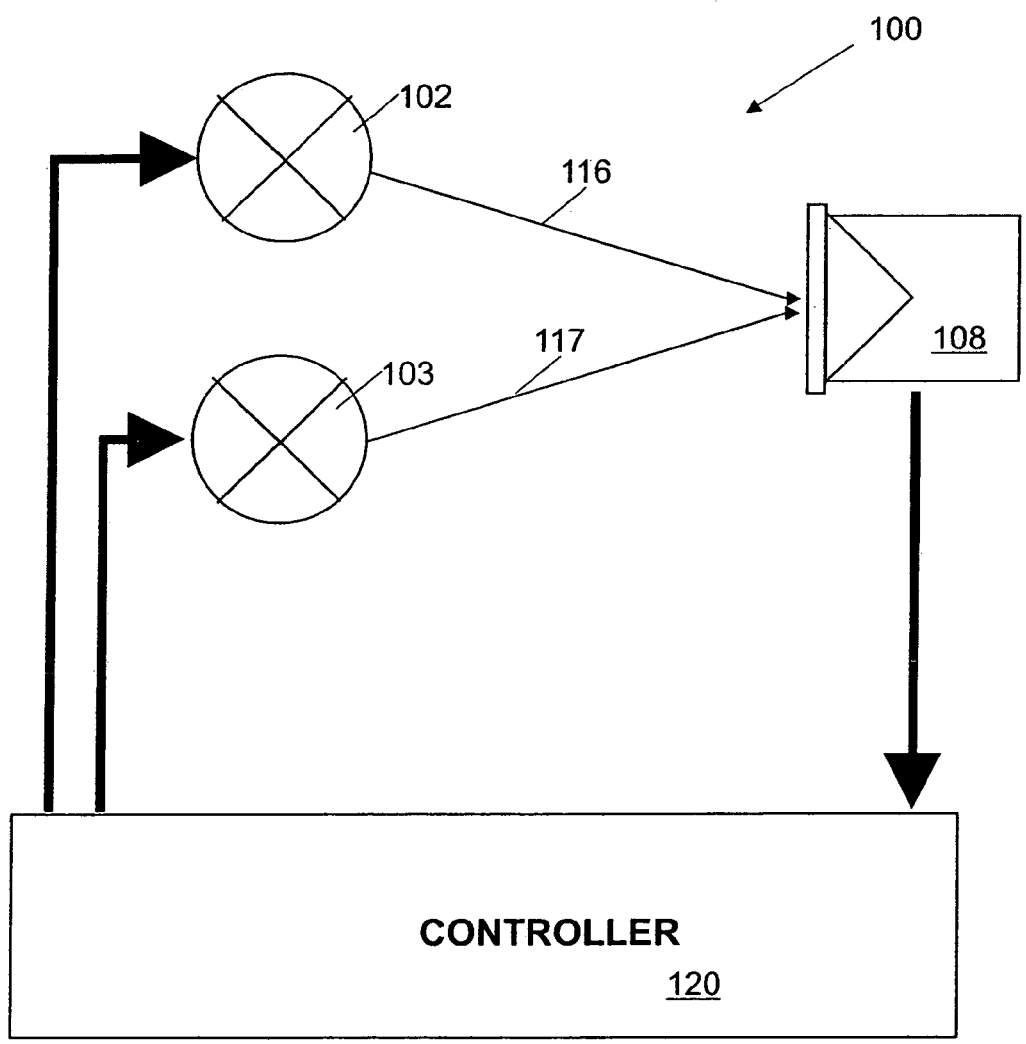
FIG. 6 is a diagrammatic view of a gas sensor arrangement according to a second embodiment of the invention.
Figure 9:
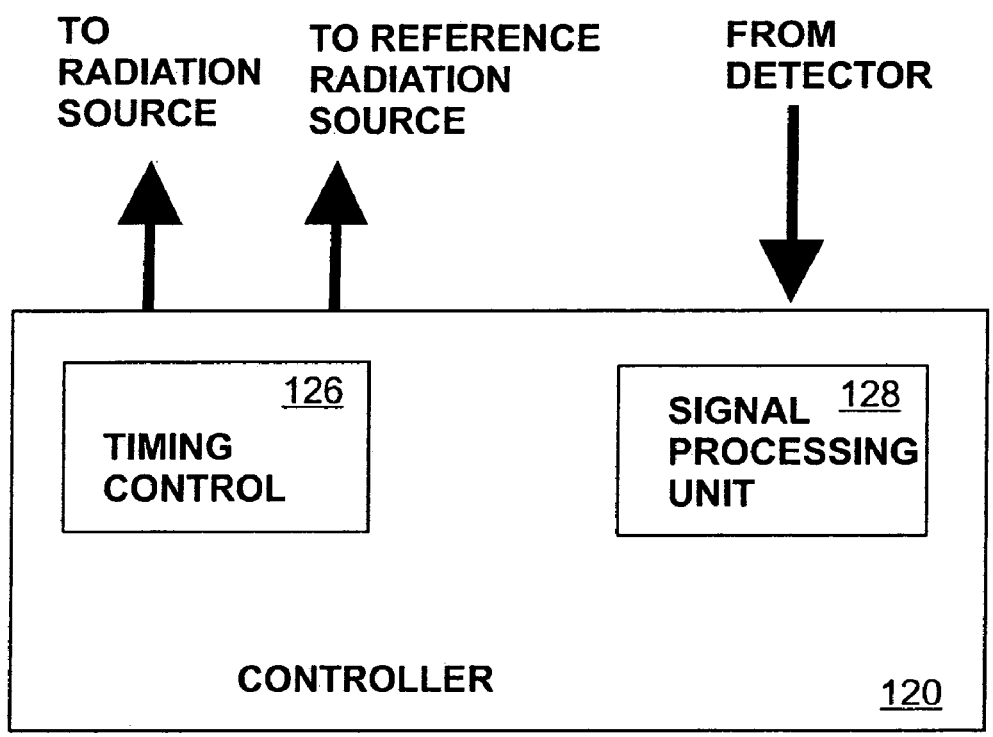
FIG. 9 is a diagrammatic view of a controller of the gas sensor arrangement shown in FIG. 6.

FIG. 6 shows a gas sensor arrangement 100 according to a second embodiment of the invention. The gas sensor arrangement 100 comprises a measuring radiation source 102 and a reference radiation source 103. The measuring and reference radiation sources 102, 103 are arranged such that a length of the paths of the radiation 116, 117 from the measuring and reference radiation sources 102, 103, respectively, to a radiation detector 108 is the same or that the measuring and reference radiation sources 102, 103 are positioned symmetrically to an axis of symmetry of a gas measuring chamber 104. As shown in FIG. 9, the controller 120 comprises a timing control 126 and a signal processing unit 128. A temperature monitoring unit and/or a timer can also be provided in order to establish the time of the respective switching from the warming-up to the measuring operation and vice versa.

The reference radiation source 103 is periodically switched-on to monitor the aging state of the measuring radiation source 102. A controller 120 detects the aging of the measuring radiation source 102, on the basis of deviations with respect to output signals of the radiation detector 108 when the reference radiation source 103 is switched-on, compared to when only the measuring radiation source 102 is switched-on. The controller 120 may then optionally correct the signals.

FIG. 8 shows a pulse sequence according to an embodiment of the invention. Curve 801 denotes the pulse sequence for the measuring radiation source 102 and curve 802 denotes the pulse sequence for the reference radiation source 103. As shown in FIG. 8, at times when the measuring radiation source 102 is not transmitting, the measuring radiation source 102 delivers usable measuring pulses and the reference radiation source 103 delivers referencing pulses, which are used to set the thermal equilibrium for the reference radiation source 103. By suitable signal processing it can be ensured that the pulses of the reference radiation source 103, which occur outside the set measuring frequency, do not influence the measuring result. At the time t=tr, the reference radiation source 103 is triggered so that it sends pulses with the measuring pulse frequency, which can be used for referencing. As the reference radiation source 103 at the time t=tr is already in the settled state, all reference values can immediately be used and the reference radiation source 103 can, for example, be switched-off again after four or five pulses.

During the time when the reference radiation source 103 delivers the usable reference pulses, it is possible for the measuring radiation source 102 to be operated with a pulse sequence which is delivered at times when the reference radiation source 103 is not transmitting. As a result, the measuring radiation source 102 does not leave thermal equilibrium and after switching-off the reference radiation source 103, its first measuring values can be used. As a result, referencing can be markedly accelerated.

FIG. 8 shows only one embodiment of the invention. According to the principles of the invention, the pulse sequences before the actual recording of measured values can also take place with altered frequencies or narrower or variable pulse widths. It is only essential that the pulse sequences are coordinated, such that only one of the radiation sources 102, 103 is emitting the radiation 116, 117 at a given time.

The invention is based on the idea that the thermal equilibrium of the gas sensor arrangement 100 can be reached more quickly when there is derivation from the conventional uniform pulse sequence of the measuring radiation source 102, Preheating necessary to reach thermal equilibrium is kept short by either widening the pulses (i.e., the pulse duty factor is altered in favor of a longer operating time) or by increasing the frequency of the pulses being increased. Thus, during the warm-up phase, energy is increasingly being delivered by the measuring radiation source 102, so that the settled state is reached more quickly.

This fundamental idea can also be applied to the gas sensor arrangement 100 in which the measuring radiation source 102 and the reference radiation source 103 are to be compared with one another during referencing. In this application, the reference radiation source 103 can advantageously be preheated with the method according to the invention, before the actual measurement of the reference values is carried out. This offers the advantage that the settled state is reached more quickly and thus the total duration of the referencing can be shortened. In safety applications, in particular, this can considerably reduce the period during which the gas sensor arrangement 110 is not operational.

In this application, the radiation 117 emitted by the reference radiation source 103, which is intended to be used to set the thermal equilibrium, merely has to be emitted during the periods when the measuring radiation source 102 is not being transmitting. Because the pulse duty factor of the pulse sequence of the measuring radiation source 102 is generally substantially smaller than one, no difficulties are thereby encountered. For example, the pulse width of the measuring radiation source 102, i.e., the operating time of the measuring radiation source 102, can be 0.4 seconds and the periodic time 2.5 seconds, which corresponds to a pulse duty factor of 0.16.

In order to be able to correct the measurement values with regard to temperature and in order to have an indication for the occurrence of the thermal equilibrium, the gas sensor arrangement 110 can also be equipped with the temperature sensor 124, which monitors the temperature of the inner wall 118 of the gas measuring chamber 104 or the temperature in the vicinity of the measuring radiation source 102.

Thus, according to the invention, by optimizing the time control of the measuring and/or referencing radiation sources 102, 103, thermal equilibrium can more rapidly be reached, and the amount of unusable measurement data can be reduced. As a result, the safety of the operation can be increased. The invention, however, is not limited to the embodiments described herein and the principles of the invention can be adapted and used for a number of other measuring and/or referencing radiation sources and radiation detectors.

We claim:

1. A gas sensor arrangement for detecting the presence or concentration of an analyte in a measuring gas, comprising:
    a gas measuring chamber having an inlet for receiving the measuring gas;
    a measuring radiation source arranged in the gas measuring chamber, the measuring radiation source emitting radiation in a non-uniform pulse sequence according to a signal from a controller; and
    a radiation detector that receives the radiation emitted from the measuring radiation source, the radiation detector sending an output signal to the controller for processing;
    wherein the non-uniform pulse sequence includes a first pulse sequence and a second pulse sequence, the first pulse sequence having a different pulse duty factor or frequency than the second pulse sequence; and
    said first pulse sequence and said second pulse sequence has a duty cycle greater than zero.

2. The gas sensor arrangement of claim 1, wherein use of the first pulse sequence or the second pulse sequence is dependant on a temperature in the gas measuring chamber.

3. The gas sensor arrangement of claim 1, further comprising a reference radiation source arranged in the gas measuring chamber, the reference radiation source emitting radiation in a non-uniform pulse sequence according to a signal from a controller, wherein only the gas measuring radiation source or the reference radiation source is emitting the radiation at a given time.

4. The gas sensor arrangement of claim 3, wherein the non-uniform pulse sequence of the reference radiation source has a different pulse duty factor or frequency than the non-uniform pulse sequence of the measuring radiation source during a given pulse sequence.

5. The gas sensor arrangement of claim 3, wherein the radiation detector receives the radiation emitted from the referencing radiation source and sends an output signal to the controller for processing.

6. The gas sensor arrangement of claim 1, further comprising a temperature sensor for monitoring a temperature of the gas measuring chamber.

7. The gas sensor arrangement of claim 1, further comprising an optical wavelength filter positioned adjacent to the radiation detector.

8. The gas sensor arrangement of claim 1, wherein the gas measuring chamber has an inner wall coated with a radiation reflective metal material.

9. The gas sensor arrangement of claim 1, wherein the inner wall is formed from a radiation reflective plastic material.

10. The gas sensor arrangement of claim 1, wherein the radiation emitted by the measuring radiation source is infrared.

* * * * *